(12) United States Patent
Wang

(10) Patent No.: US 11,433,128 B2
(45) Date of Patent: Sep. 6, 2022

(54) CELL SURFACE ANCHORING ANTIGEN CONJUGATES TO TREAT CANCER

(71) Applicant: Tianxin Wang, Walnut Creek, CA (US)

(72) Inventor: Tianxin Wang, Walnut Creek, CA (US)

( * ) Notice: Subject to any disclaimer, the term of this patent is extended or adjusted under 35 U.S.C. 154(b) by 355 days.

(21) Appl. No.: 15/945,741

(22) Filed: Apr. 5, 2018

(65) Prior Publication Data

US 2018/0311335 A1  Nov. 1, 2018

Related U.S. Application Data

(60) Provisional application No. 62/482,982, filed on Apr. 7, 2017.

(51) Int. Cl.
| | |
|---|---|
| *A61K 39/02* | (2006.01) |
| *A61K 31/4745* | (2006.01) |
| *A61K 31/575* | (2006.01) |
| *A61P 35/00* | (2006.01) |
| *A61K 39/00* | (2006.01) |

(52) U.S. Cl.
CPC ........ *A61K 39/107* (2013.01); *A61K 31/4745* (2013.01); *A61K 31/575* (2013.01); *A61K 39/0011* (2013.01); *A61P 35/00* (2018.01); *A61K 2039/55561* (2013.01); *A61K 2039/60* (2013.01); *A61K 2039/6018* (2013.01); *A61K 2039/627* (2013.01)

(58) Field of Classification Search
None
See application file for complete search history.

(56) References Cited

U.S. PATENT DOCUMENTS

| | | | |
|---|---|---|---|
| 8,637,468 B2 * | 1/2014 | Peterson | A61K 47/554 514/20.9 |
| 2014/0112975 A1 * | 4/2014 | Kiessling | A61K 47/543 424/450 |

FOREIGN PATENT DOCUMENTS

| | | | | |
|---|---|---|---|---|
| WO | WO-2013166110 A1 * | 11/2013 | | A61K 47/6869 |
| WO | 2016146261 | * | 9/2016 | |

OTHER PUBLICATIONS

Boonyarattanakalin et al., J. Am. Chem. Soc., 2004, 126 (50), p. 16379-16386 (Year: 2004).*

* cited by examiner

*Primary Examiner* — Karl J Puttlitz

(57) ABSTRACT

This disclosure provides cell surface anchoring antigen conjugates, formulations comprising cell surface anchoring antigen conjugates, and methods of using the same for treating cancer.

6 Claims, 11 Drawing Sheets

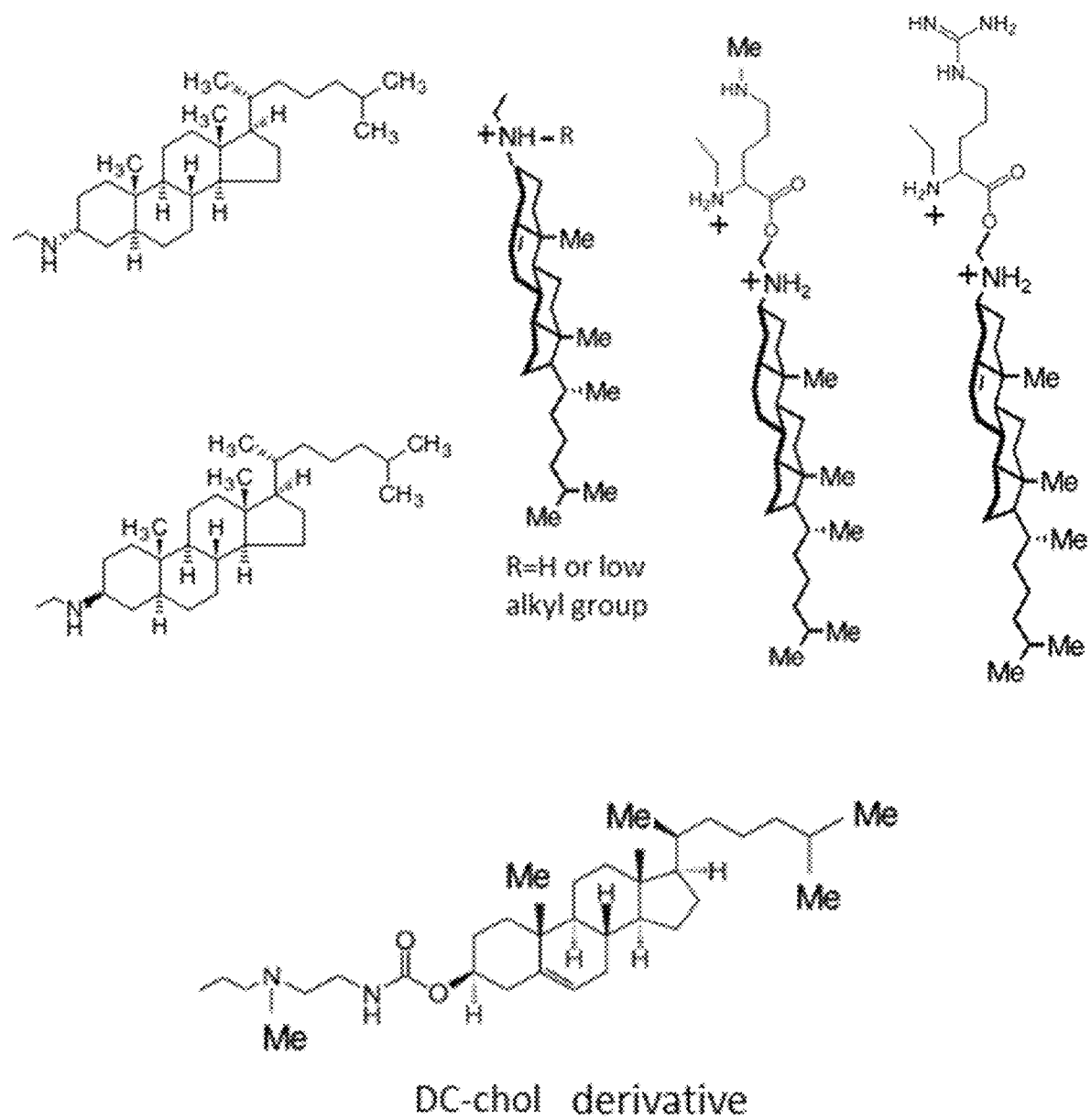
FIG 3, continued

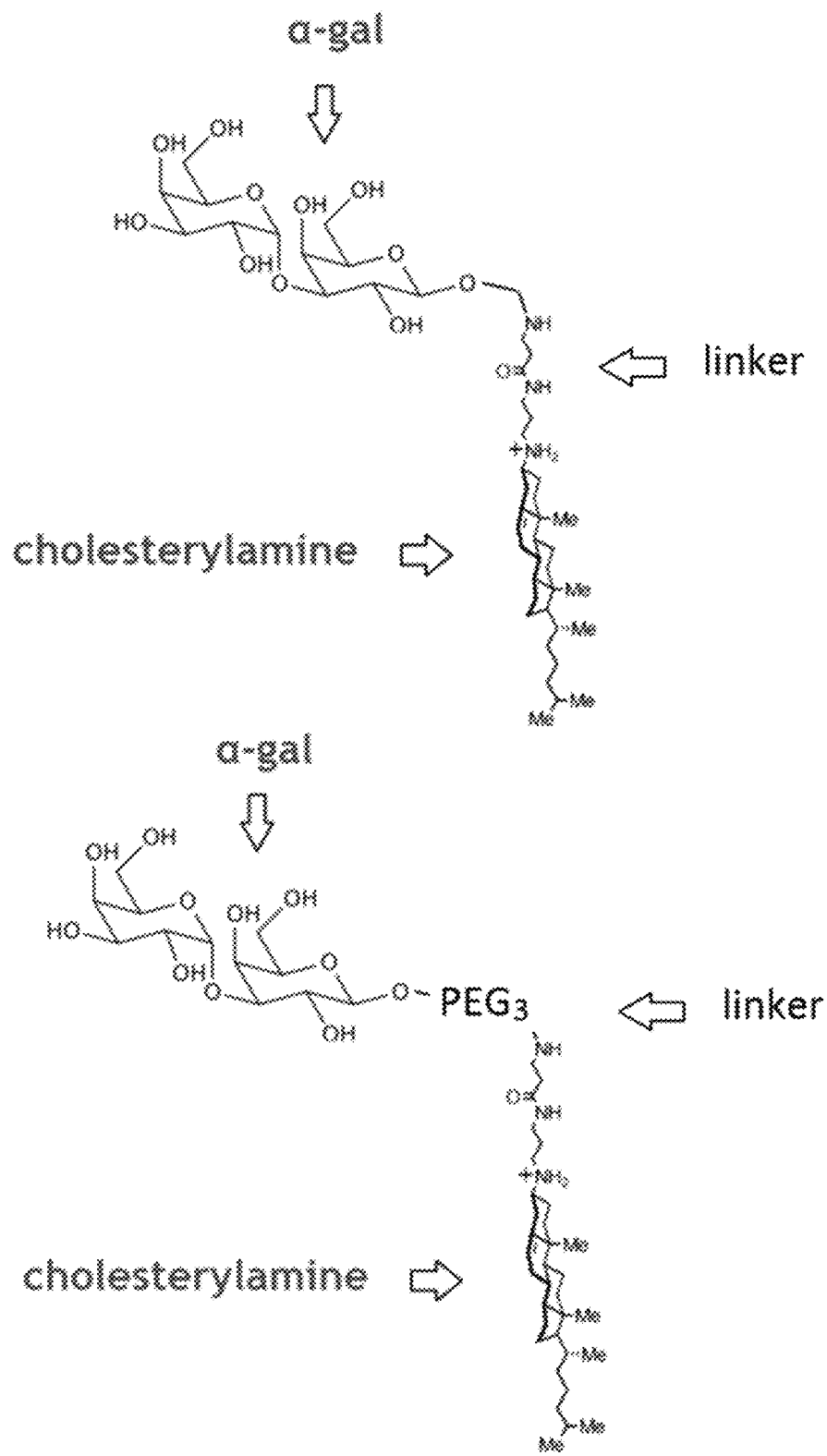
FIG. 4, continued

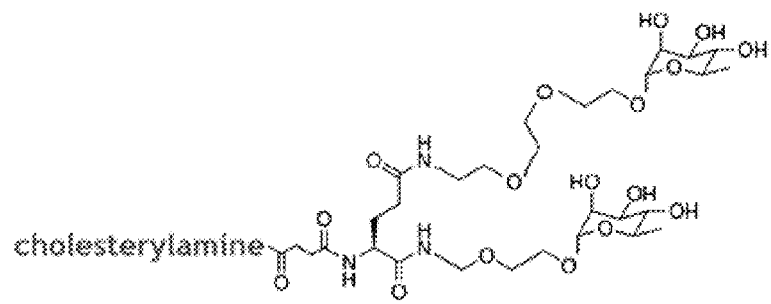
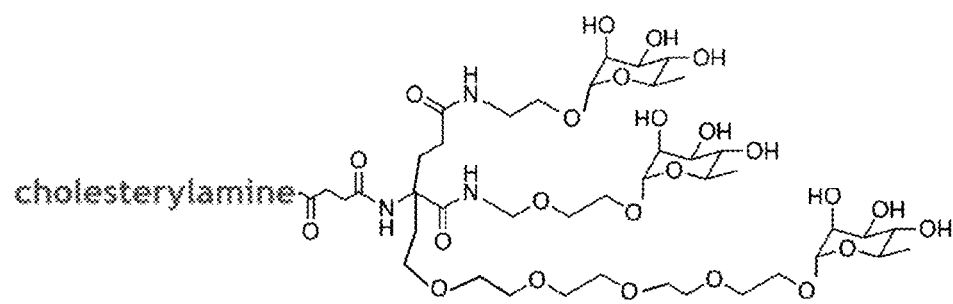
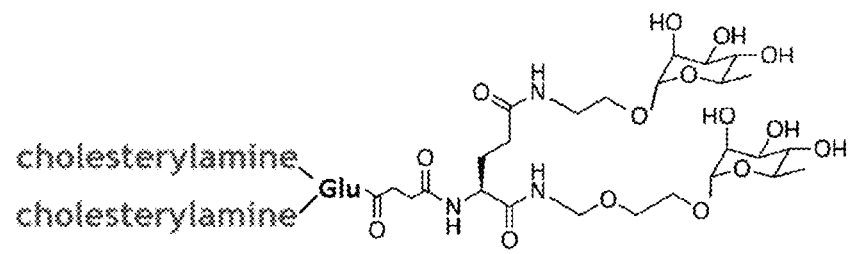
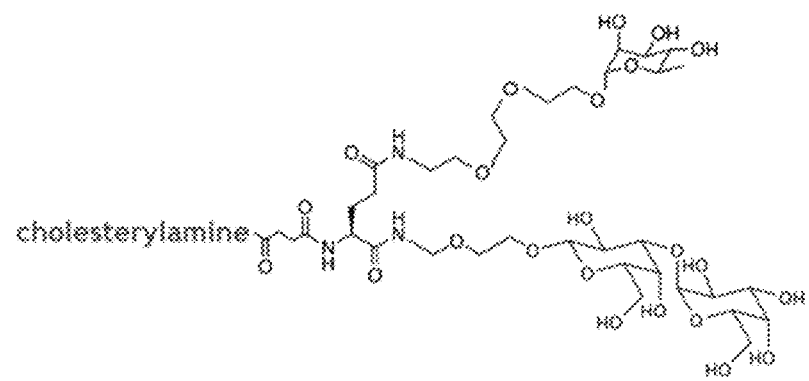
FIG. 4, continued

DOTMA derivative

DOTAP derivative

Didodecyldimethylammonium derivative

R=H or low alkyl group

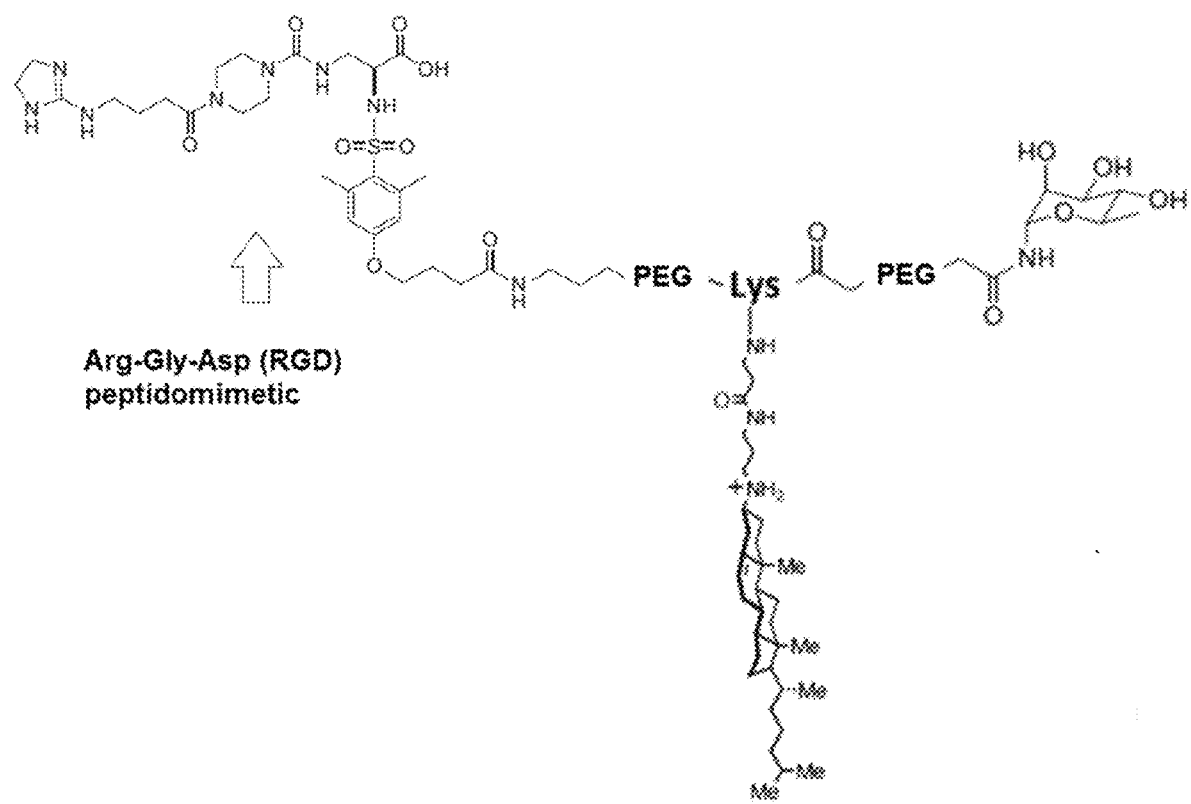
FIG. 7, continued

CELL SURFACE ANCHORING ANTIGEN CONJUGATES TO TREAT CANCER

CROSS-REFERENCE TO RELATED APPLICATION

This application claims priority to U.S. Provisional Patent Application 62/482,982 filed on Apr. 7, 2017. The entire disclosure of the prior application is considered to be part of the disclosure of the instant application and is hereby incorporated by reference.

FIELD

This disclosure provides cell surface anchoring antigen conjugates, formulations comprising cell surface anchoring antigen conjugates, and methods of using the same for treating cancer.

BACKGROUND

The U.S. Food and Drug Administration has approved several checkpoint inhibitors for the treatment of various cancers over the last decade. Checkpoint inhibitors work by exposing cancer cells that have hidden from the immune system. Cancer cells deceive immune cells by sending signals at certain checkpoints that indicate they are not harmful. If not for these checkpoints, T-cells would attack healthy cells. Immunotherapy drugs disrupt the cancer cells' signals, exposing them to the immune system for attack.

Researchers continue to search for new drugs, as well as combinations thereof with other known checkpoint inhibitor drugs, for use in treating tumors, as improved treatment results for patients with breast cancer, gastric cancer and other advanced cancers are needed.

SUMMARY

The present disclosure is directed to compounds, compositions and methods for treating cancer by treating and/or inhibiting tumors in a patient. In certain embodiments, provided is a cell surface anchoring antigen conjugate comprising at least one antigen covalently bonded to 3β-cholesterylamine, or an analogue or derivative thereof, optionally via linker. Also provided are pharmaceutical compositions comprising a cell surface anchoring antigen conjugate, such as, but not limited to, those described herein, and a Toll-like receptors (TLR) agonist. Suitable Toll-like receptors (TLR) agonists include, but are not limited to, CpG ODN (CpG oligodeoxynucleotide), polyinosinic: polycytidylic acid (poly IC), imiquimod, and the like, or a mixture thereof.

In certain embodiments, the present disclosure is directed to a method of treating and/or inhibiting a tumor and its metastasis, comprising administering to a patient in need thereof a therapeutically effective amount of a cell surface anchoring antigen conjugate or a pharmaceutical composition as described herein.

BRIEF DESCRIPTION OF THE DRAWINGS

Certain aspects of the present disclosure can be viewed by the accompanying figure. Included is the following.

DETAILED DESCRIPTION

Figure 1A:
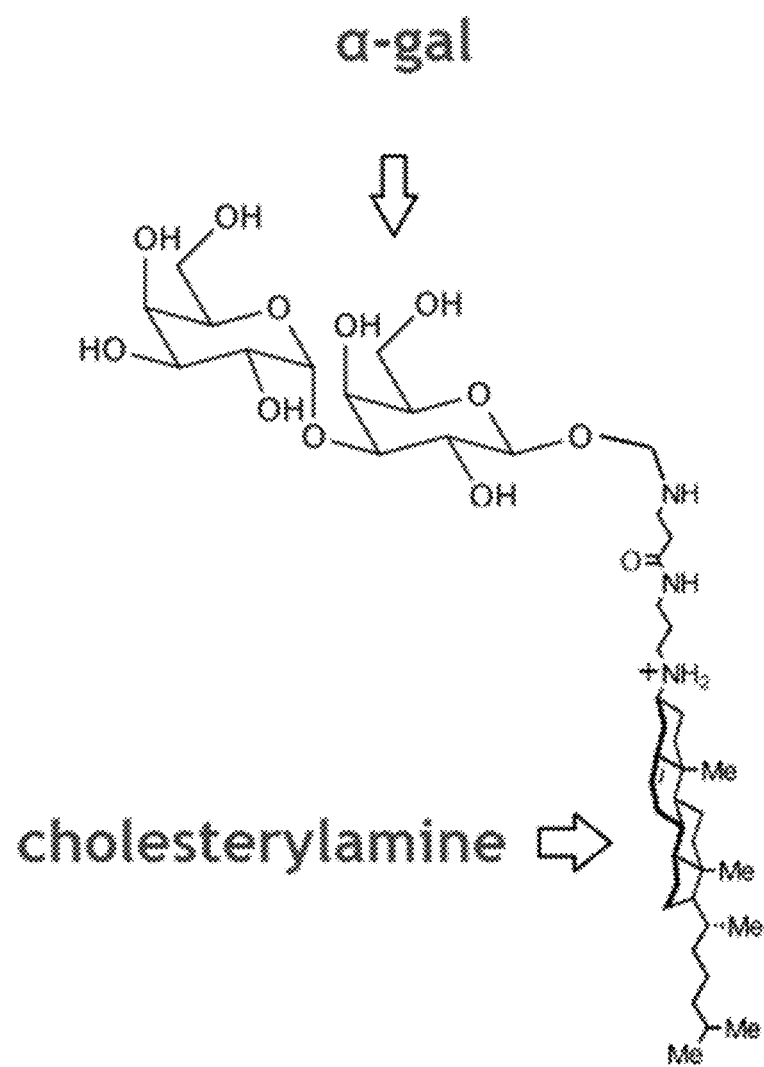
FIG. 1 shows exemplary conjugates. Panel A shows an α-gal-cholesterylamine conjugate. Panel B shows a L-rhamnose-cholesterylamine conjugate with folic acid incorporated.
Figure 1:
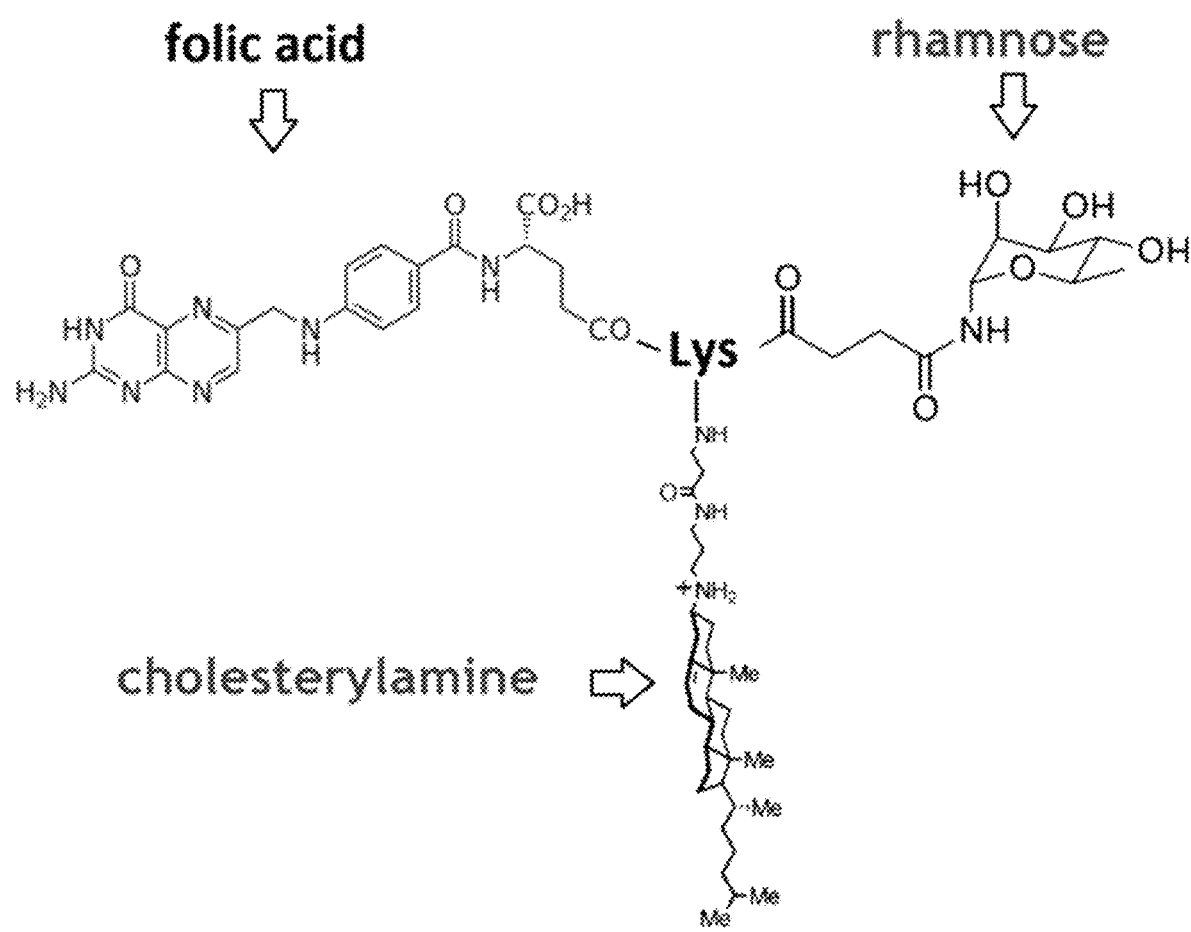

It is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Definitions

Unless defined otherwise, all technical and scientific terms used herein have the same meaning as commonly understood by one of ordinary skill in the art to which this disclosure belongs. As used herein the following terms have the following meanings.

It must be noted that as used herein and in the appended claims, the singular forms "a", "an", and "the" include plural referents unless the context clearly dictates otherwise. Thus, for example, reference to "an adjuvant" includes a plurality of adjuvants.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) claimed. "Consisting of" shall mean excluding more than trace elements of other ingredients and substantial method steps. Embodiments defined by each of these transition terms are within the scope of this disclosure.

The term "about" when used before a numerical designation, e.g., temperature, time, amount, and concentration, including range, indicates approximations which may vary by (+) or (−) 10%, 5% or 1%.

As used herein, the term "treating" refers to preventing, curing, reversing, attenuating, alleviating, minimizing, inhibiting, suppressing and/or halting a disease or disorder, including one or more clinical symptoms thereof.

As used herein, the term "composition" refers to a preparation suitable for administration to an intended patient for therapeutic purposes that contains at least one pharmaceutically active ingredient, including any solid form thereof. In certain embodiments, the composition is formulated as an injectable formulation. In certain embodiments, the composition is formulated as a film, gel, patch, or liquid solution.

As used herein, the term topically refers to administering a composition non-systemically to the surface of a tissue (e.g., a tumor) and/or organ (internal or, in some cases, external; through a catheter) to be treated, for local effect.

As used herein, the term "pharmaceutically acceptable" indicates that the indicated material does not have properties that would cause a reasonably prudent medical practitioner to avoid administration of the material to a patient, taking into consideration the disease or conditions to be treated and the respective route of administration. For example, it is commonly required that such a material be essentially sterile.

As used herein, the term "pharmaceutically acceptable carrier" refers to pharmaceutically acceptable materials, compositions or vehicles, such as a liquid or solid filler, diluent, excipient, solvent or encapsulating material, involved in carrying or transporting any supplement or composition, or component thereof, from one organ, or portion of the body, to another organ, or portion of the body, or to deliver an agent to the desired tissue or a tissue adjacent to the desired tissue.

As used herein, the term "formulated" or "formulation" refers to the process in which different chemical substances, including one or more pharmaceutically active ingredients, are combined to produce a dosage form. In certain embodiments, two or more pharmaceutically active ingredients can be coformulated into a single dosage form or combined dosage unit, or formulated separately and subsequently combined into a combined dosage unit. A sustained release formulation is a formulation which is designed to slowly release a therapeutic agent in the body over an extended period of time, whereas an immediate release formulation is a formulation which is designed to quickly release a therapeutic agent in the body over a shortened period of time.

As used herein, the term "delivery" refers to approaches, formulations, technologies, and systems for transporting a pharmaceutical composition in the body as needed to safely achieve its desired therapeutic effect. In some embodiments, an effective amount of the composition is formulated for intratumoral injection into the patient (e.g., intratumoral delivery).

As used herein, the term "solution" refers to solutions, suspensions, emulsions, drops, ointments, liquid wash, sprays, liposomes which are well known in the art. In some embodiments, the liquid solution contains an aqueous pH buffering agent which resists changes in pH when small quantities of acid or base are added. In certain embodiments, the liquid solution contains a lubricity enhancing agent.

As used herein, the term "pH buffering agent" refers to an aqueous buffer solution which resists changes in pH when small quantities of acid or base are added to it. pH Buffering solutions typically comprise of a mixture of weak acid and its conjugate base, or vice versa. For example, pH buffering solutions may comprise phosphates such as sodium phosphate, sodium dihydrogen phosphate, sodium dihydrogen phosphate dihydrate, disodium hydrogen phosphate, disodium hydrogen phosphate dodecahydrate, potassium phosphate, potassium dihydrogen phosphate and dipotassium hydrogen phosphate; boric acid and borates such as, sodium borate and potassium borate; citric acid and citrates such as sodium citrate and disodium citrate; acetates such as sodium acetate and potassium acetate; carbonates such as sodium carbonate and sodium hydrogen carbonate, etc. pH Adjusting agents can include, for example, acids such as hydrochloric acid, lactic acid, citric acid, phosphoric acid and acetic acid, and alkaline bases such as sodium hydroxide, potassium hydroxide, sodium carbonate and sodium hydrogen carbonate, etc. In some embodiments, the pH buffering agent is a phosphate buffered saline (PBS) solution (i.e., containing sodium phosphate, sodium chloride and in some formulations, potassium chloride and potassium phosphate).

Compounds

Provided herein are cell surface anchoring antigen conjugates comprising 3β-cholesterylamine, or an analogue or derivative thereof, wherein the 3β-cholesterylamine comprises at least one antigen covalently bonded thereto. The cell surface anchoring antigen conjugate works as a cancer cell lysing agent and enhances tumor antigen presentation. The 3β-cholesterylamine is the cell surface anchoring molecule in the conjugate. In certain embodiments, the antigen is bonded to the 3β-cholesterylamine via a linker. It is contemplated that the cell surface anchoring antigen conjugates described therein will exhibit a longer cell surface half-life than the equivalent fatty acid-based antigen conjugates. In these embodiments, the at least one antigen is covalently bonded to 3β-cholesterylamine via the amine.

The antigen used in the conjugate can be any antigen, and is in certain embodiments, a molecule that is the antigen of existing antibody in a patient or antigen of TCR (T-cell receptor) of T cell in a patient, which is referred to as a native antigen. Suitable native antigens include, but are not limited to, galactose-alpha-1,3-galactose (α-gal), L-rhamnose, Forssman disaccharide, phosphorylcholine (PC), DNP (dinitrophenyl), or a combination thereof. Endogenous anti-Gal antibody binds to alpha-gal epitope, is highly abundant in humans, accounting for about 1% of total antibody in serum, resulting from the α-gal antigen of the microbes in the GT tract. Native α-gal immunity plays a key role in xenotransplantation rejection. L-rhamnose antigen is an alternative to α-gal, and may also be employed in the cell surface anchoring antigen conjugates disclosed herein. Endogenous anti-L-rhamnose antibody is abundant in humans with high affinity.

In some embodiments, the cell surface anchoring antigen conjugate of the current invention has the following formula, which is a conjugate of native antigen with cell surface anchoring molecule via an optional linker:

Native Antigen-Optional Linker-Cell Surface Anchoring Molecule

Figure 2:
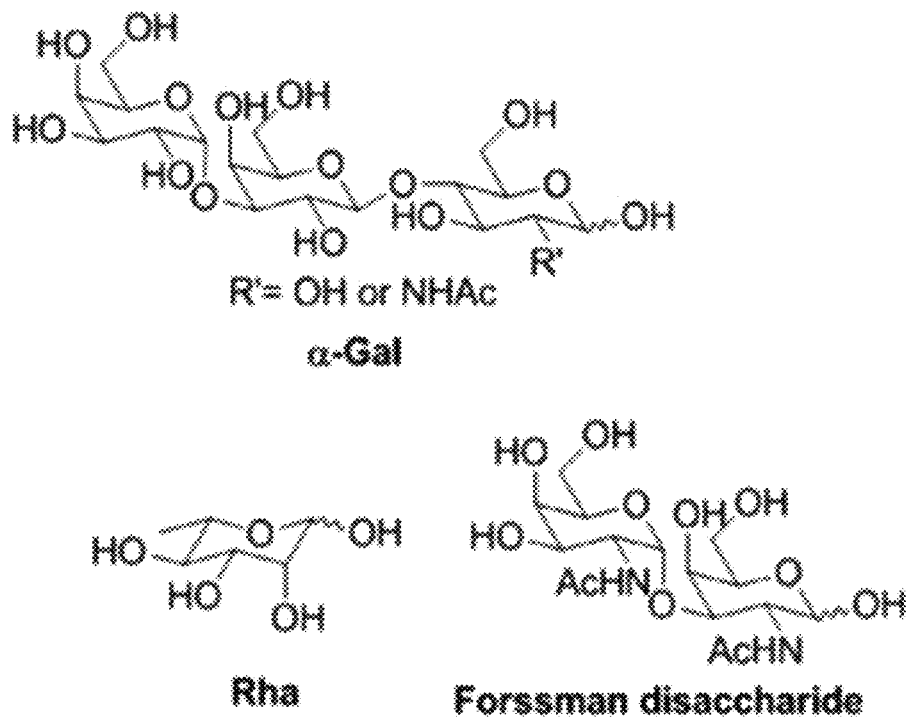
FIG. 2 shows exemplary antigens for use in the cell surface anchoring antigen conjugates.

Exemplary α-gal native antigens suitable for incorporation into the cell surface anchoring antigen conjugates can be found and readily adopted from the literature (see, e.g., US 2010/0145015, U.S. Pat. No. 7,820,628, WO2015/170121, U.S. Pat. No. 8,440,198, Oncoimmunology, 2013 Jan. 1; 2(1):e22449; Anticancer Res. 2012 September; 32(9): 3861-8; Cancer Immunol Immunother. 2016; 65(8):897-907). Exemplary L-rhamnose native antigens suitable for incorporation into the cell surface anchoring antigen conjugates can be found and readily adopted from literature (see, e.g., US 2014/0112975; Chembiochem. 2014; 15(10):1393-8; ACS Chem Biol. 2011; 6(2):185-91; ACS Chem Biol. 2016; 11(5):1205-9). The GalNAc-R(1,3)-GalNAc (Forssman disaccharide) native antigen suitable for incorporation into the cell surface anchoring antigen conjugates can be found and readily adopted from patent application US 2013/0149331. The phosphorylcholine (PC) native antigen suitable for incorporation into the cell surface anchoring antigen conjugates can be found and readily adopted from ACS Chem. Biol. 2013, 8, 2404-2411. See FIG. 2.

The alpha-gal lipid conjugates or L-rhamnose lipid conjugates described in the literature can also be used as cell surface anchoring antigen conjugate described herein to be co-injected into tumor or co-formulated with immune function enhancing agent type composition for intratumoral injection or other routes.

In addition to α-gal, L-rhamnose, Forssman disaccharide and phosphorylcholine (PC), other antigens which have T-cell immunity or B-cell immunity may also be used in the cell surface anchoring antigen conjugate, which can be endogenous or induced by vaccination. Another example of an endogenous antigen is dinitrophenyl (DNP). The induced antibody or antigen specific effector T-cell can be generated with vaccination. For example, most newborns receive the antituberculosis vaccine BCG, the oral poliovirus vaccine (OPV) and the anti-hepatitis B vaccine (HBVac) resulting in B-cell or T-cell immunity against these antigens. One can use these antigens to prepare the conjugate. In practice, the patient can be first tested for his antigen reactivity and then you can select the antigen having strong B-cell or T-cell immunity to prepare the conjugate. The patient can then be administered this personalized conjugate to treat a particular disease (e.g. cancer or auto immune disease). One can also inject a patient with a vaccine for a special antigen (e.g. a non-native peptide antigen conjugated to keyhole limpet hemocyanin (KLH), administered with boosters) to allow the patient to develop T-cell immunity or B-cell immunity against this antigen and then use this antigen to prepare the conjugate described herein for disease treatment. Another example utilizing native immunity is to use the blood type antigen instead of α-gal to build the conjugate (e.g., ABO antigen). For example, for patient having a blood type of group A, the conjugate can utilize B antigen; for patient having a blood type of group B, the conjugate can utilize A antigen; for patient having a blood type of group O, the conjugate can utilize either A or B antigen or their combination. T-cell antigen can be the MHC-peptide complex form. When alpha-gal containing conjugate is used to treat cancer, the patient can be given a vaccine that can induce/increase anti alpha-gal antibody production/efficacy (e.g. alpha-gal/KLH conjugate with booster) prior and/or during the treatment. This will increase the production of anti-alpha gal antibody and increase the antibody's affinity/potency. This vaccination strategy can also be used in the methods described herein using other native antigen such as L-rhamnose or dinitrophenyl to recruit endogenous antibodies in order to treat diseases and boost the corresponding antibody potency prior to or during the treatment.

In certain embodiments, the cell surface anchoring antigen conjugate described herein comprises more than one antigen, which can be either more than one of the same or a combination of different antigens. An optional linker or spacer can be used to connect the antigen to the cell surface anchoring molecule. In such embodiments, the linker can be linear or branched. In certain embodiments, the linker is a peptide or polyethylene glycol-containing moiety having a molecular weight of less than about 1500. In certain embodiments, the linker comprises an amino acid or a peptide sequence comprising one or more Lys, Arg, or other positively charged amino acid. In certain embodiments, the amine of the cholesterylamine in the conjugate can be converted to quaternary ammonium.

Figure 3:
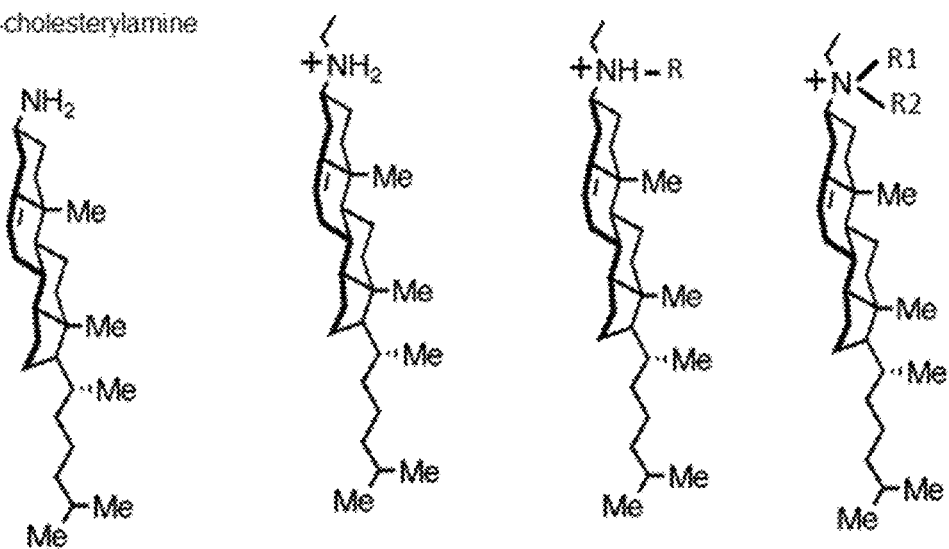
FIG. 3 shows examples of 3β-cholesterylamine, 3β-cholesterylamine containing moiety and their derivatives used for the conjugate.

FIG. 3 shows examples of 3β-cholesterylamine, 3β-cholesterylamine containing moiety and their derivatives or analogues used for the conjugate. Exemplary derivatives include, but are not limited to, compounds where the amine group can be substituted with linear or branched alkyl group or alkenyl group or alkynyl or aryl group containing 1 to 30 carbons, such as methyl, ethyl or other low alky groups (e.g., R, $R^1$, $R^2$ in FIG. 3). The 3β-cholesterylamine can also be further conjugated with a positive charge group containing moiety, such as an arginine. The double bond alkenyl —C=C— group in the cholesterylamine can be replaced with a saturated alkyl —C—C-group, resulting in a cholestane derivative. In some embodiments, the cholesterylamine is substituted by 3-amino triterpenes, including cholestane, cholestadiene and cholestane. Further, it is contemplated that the 3-amine group of the cholesterylamine can be either in the alpha or beta configuration.

Figure 4:
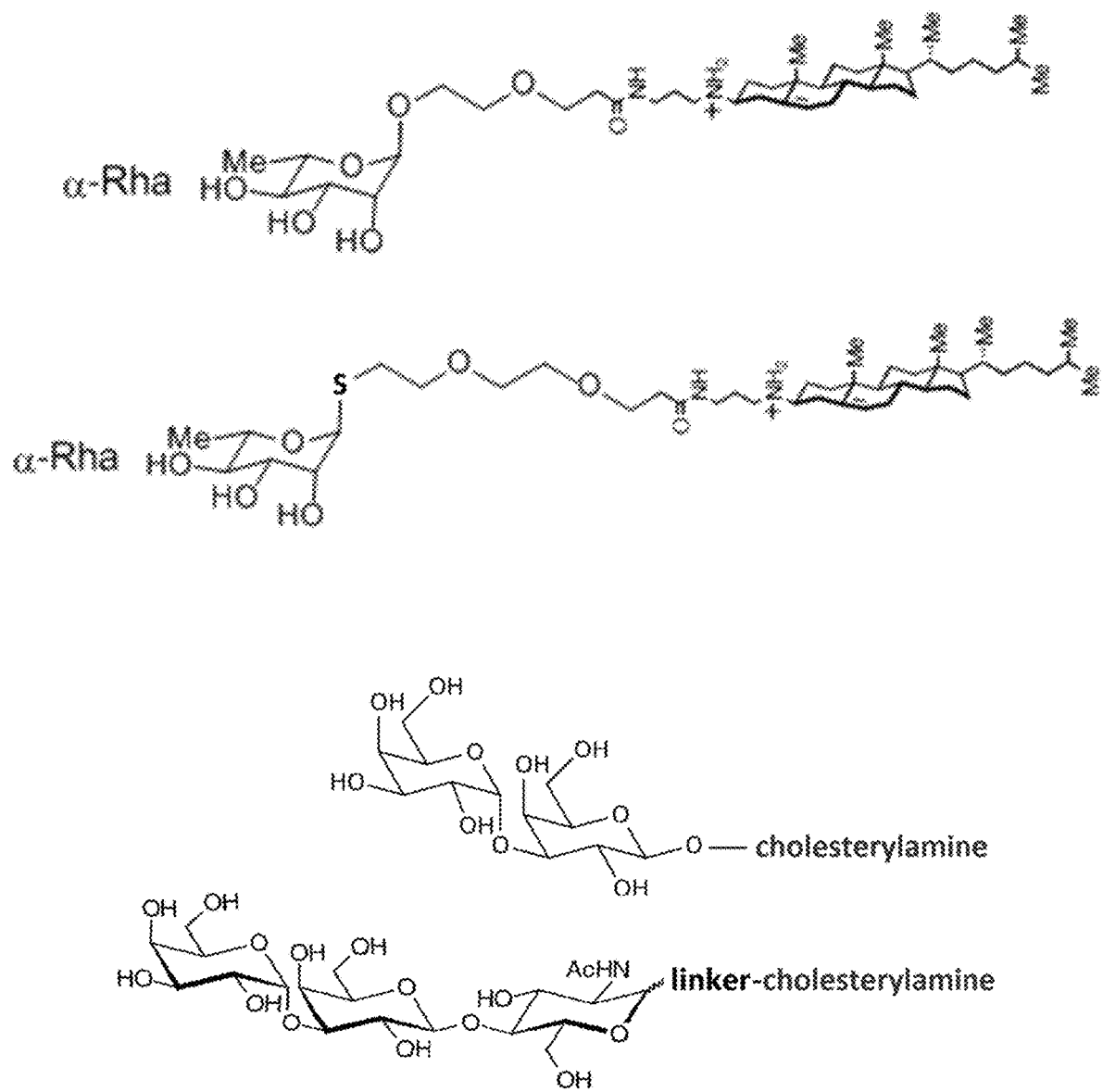
FIG. 4 shows exemplary structures of the cell surface anchoring antigen conjugate.

Exemplary structures of the cell surface anchoring antigen conjugate include α-gal-cholesterylamine, L-rhamnose-cholesterylamine, α-gal-linker-cholesterylamine, L-rhamnose-linker-cholesterylamine, L-rhamnose oligomer-linker(optional)-cholesterylamine, α-gal oligomer-linker(optional)-cholesterylamine, Forssman disaccharide-linker(optional)-cholesterylamine, α-gal-linker-cholesterylamine-L-rhamnose. The bond used to connect the carbohydrate based native antigen preferably is glycosidic bond such as S-, N-, C-, and O-glycosidic bonds (FIG. 4). FIG. 4 also shows an exemplary α-gal based conjugate design: alpha-galactosyl-(optional linker)-cholesterylamine, which will allow it bind with endogenous anti-Gal antibody and therefore eliminate the anchored cells.

More than one unit of native antigen, more than one type of native antigens and more than one unit of cell surface anchoring molecule such as cholesterylamine can be incorporated in the conjugate (FIG. 4). They can be either in monomer or oligomer format within the conjugate. As shown in FIG. 4 they can also be conjugated to a soluble polymer backbone (e.g. dextran, poly peptide, poly acrylic acid or the like).

Figure 5:
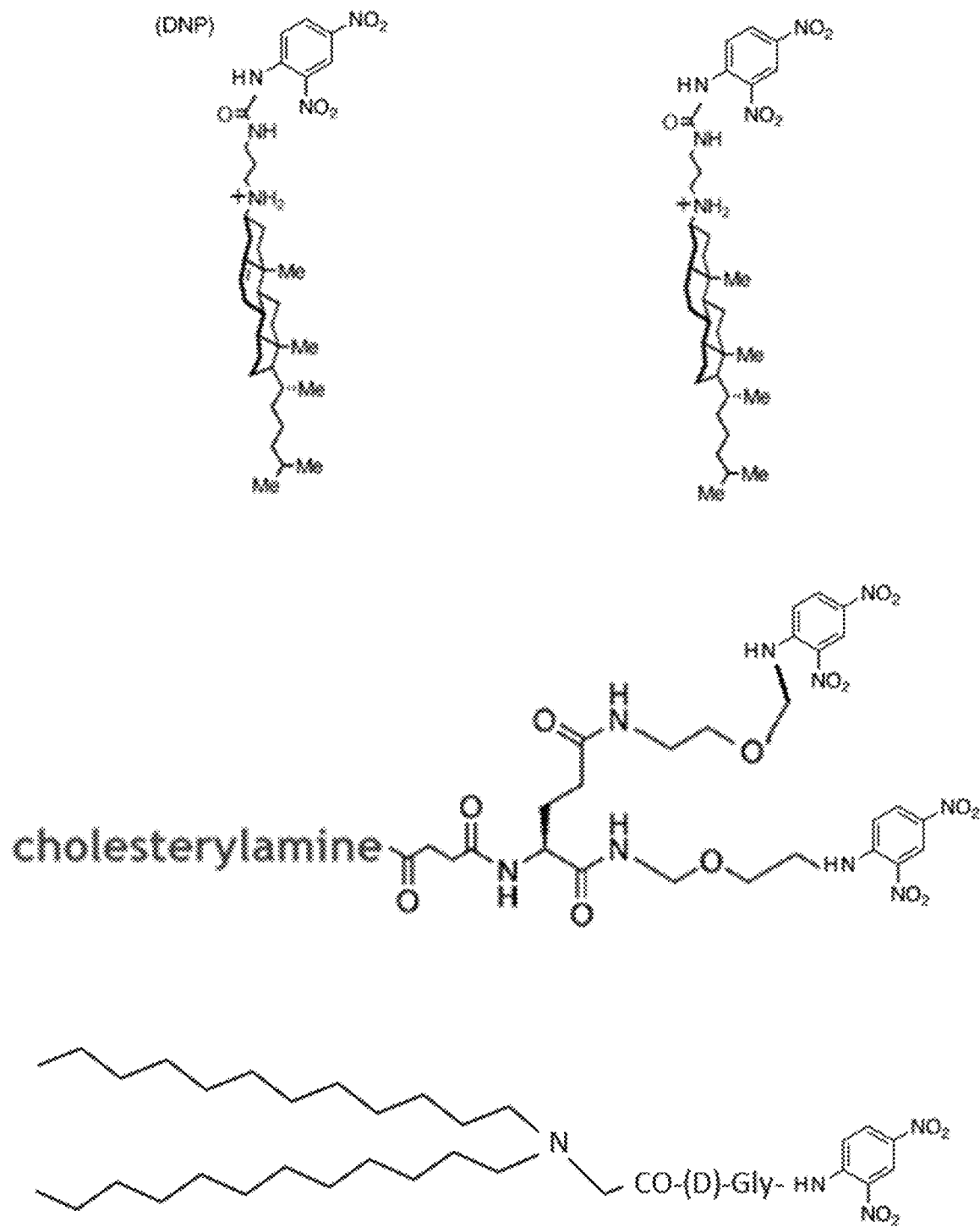
FIG. 5 shows further exemplary structures of the cell surface anchoring antigen conjugate.

As described previously, other endogenous antigen such as Forssman disaccharide, phosphorylcholine (PC), DNP (dinitrophenyl) can also be used to make the conjugate. Examples are shown in FIG. 5.

Figure 6:
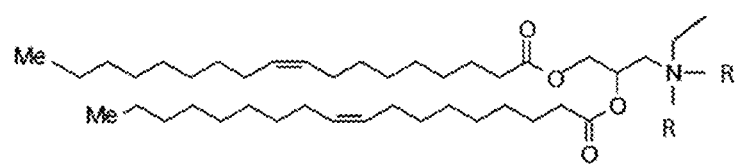
FIG. 6 shows exemplary lipid moieties for use in the cell surface anchoring antigen conjugates.
Figure 6:
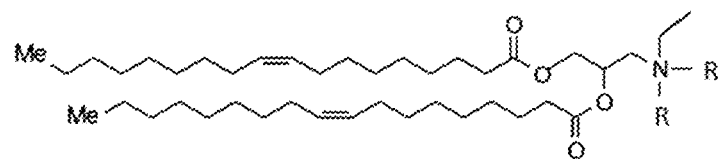
Figure 6:
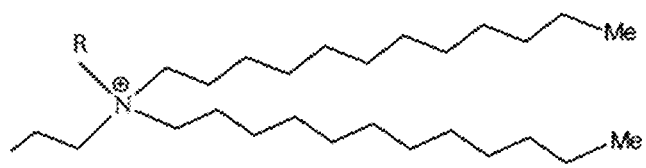

The cell surface anchoring molecule portion of the conjugate may also comprise compounds other than cholesterylamine, such as lipid molecules and cell surface anchoring peptides. Examples of the lipid molecule suitable for use in the cell surface anchoring antigen conjugates include phospholipids glycerolipids, glycerophospholipids, sphingolipids, ceramides, glycerophosphoethanolamine, sterols or steroids. In certain embodiments, the cell surface anchoring molecule is cationic lipid where the conjugation is at the cationic end containing secondary, tertiary or quaternary amine group. The FIGS. 5, 6 show additional examples of cell surface anchoring molecule/moiety. In certain embodiments, rhamnolipids including mono-rhamnolipids and di-rhamnolipids produced by *Pseudomonas aeruginosa* or other microorganisms, α-galactosylceramide (α-GalCer), α-glucosylceramide (α-GlcCer), α-glucuronylceramide, α-galacturonylceramide and their analogue/derivatives can also be used as cancer cell lysing agent. The α-galactosylceramide (α-GalCer), α-glucosylceramide (α-GlcCer), α-glucuronylceramide and α-galacturonylceramide are T cell antigens.

Figure 7:
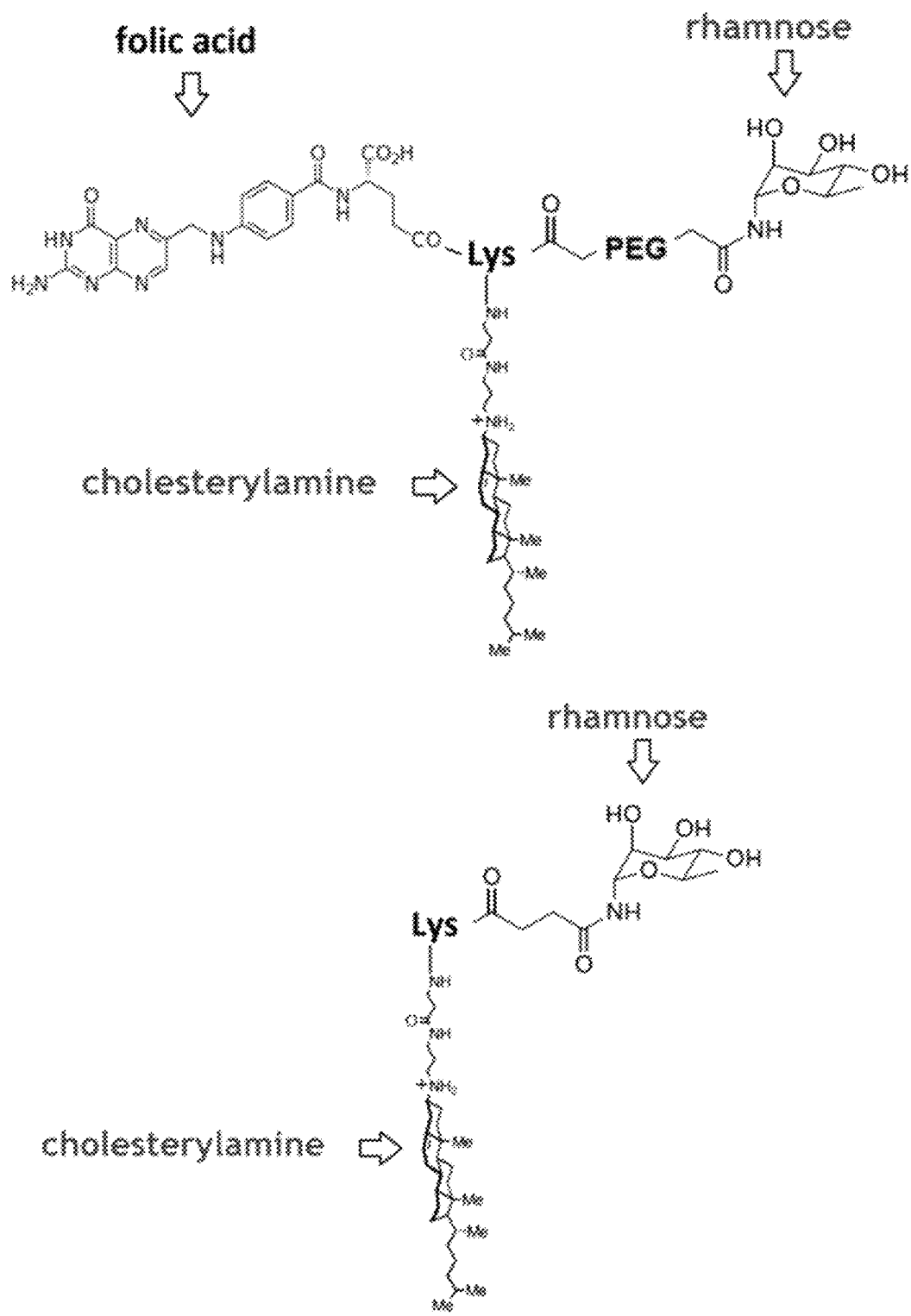
FIG. 7 shows further exemplary structures of the cell surface anchoring antigen conjugate.

The conjugate can further comprise a cancer cell binding domain to increase its targeting to a cancer cell, which will allow intravenous (IV) injection instead of intratumoral injection. Small molecule ligand for cancer such as folic acid and RGD peptide/peptidomimetic can be used for cancer targeting (e.g. those described in Curr Med Chem. 2014; 21(14):1618-30; Current pharmaceutical design 16(9):1040-54 and Journal of Amino Acids, Volume 2012 (2012)). Folic acid or RGD peptide (arginylglycylaspartic acid) can be incorporated into the conjugate to increase cancer targeting. Multi-valency strategy and affimer type affinity ligand can also be used. Accordingly, in certain embodiments, the cell surface anchoring antigen conjugate comprises a cancer cell binding domain, such as folic acid, RGD peptide, RGD peptidomimetic, or a TGF-α, GnRH, EGFR or VEGF antagonist. Examples include alpha-gal-(optional linker)-EGF, alpha-gal-(optional linker)-VEGF, alpha-gal-(optional linker)-TGF-α, alpha-gal-GnRH. Affinity ligands that bind with EGFR or VEGFR without activating them, e.g. EGFR or VEGF antagonist, are used to prepare the conjugate. For example, decorin, VEGF165b, or a VEGF antagonist as described in PCT/CA2010/000275 can be used to prepare the conjugate instead of using native VEGF that can activate VEGFR for angiogenesis. The conjugation of other native antigen such as L-rhamnose with peptide/protein/small molecules (e.g. folic acid, VEGF or their derivatives/mimics such as VEGF165b) are also provided. Examples include folic acid-optional linker-alpha-gal, VEGF165b-optional linker-alpha-gal, VEGF-optional linker-alpha-gal, folic acid-optional linker-alpha L-rhamnose, VEGF165b-optional linker-alpha L-rhamnose, VEGF-optional linker-alpha-L-rhamnose. In certain embodiments, the cell surface anchoring antigen conjugate does not contain lipid or cholesterylamine. Further examples are shown in FIG. 7.

Formulations

Also provided are compositions and formulations for use as in situ cancer vaccines to promote a strong immune response against cancer cells. In one embodiment, provided is a pharmaceutical composition comprising a cell surface anchoring antigen conjugate and an immune function enhancing agent. Examples of suitable immune function enhancing agent include pattern recognition receptor (PRR) ligands, RIG-I-Like receptor (RLR) ligands, Nod-Like receptor (NLR) ligands, C-Type Lectin Receptors (CLR) ligands, and Toll-like receptor ligands such as a TLR3 ligand, a TLR4 ligand, a TLR5 ligand, a TLR7/8 ligand, a TLR9 ligand, or a combination thereof. The immune function enhancing agent can be a vaccine adjuvant. Preferably the Toll-like receptor ligand is a Toll-like receptors (TLR) agonist. Exemplary Toll-like receptors (TLR) agonists include, but are not limited to, CpG (CpG ODNs), poly IC, imiquimod, or a combination thereof. For these formulations, the cell surface anchoring antigen conjugate can be any of those described herein above, or any known in the art. For example. In certain embodiments, the cell surface anchoring antigen conjugate comprises a antigen (e.g., monosaccharide or oligosaccharide moiety) covalently bonded to a lipophilic cell surface anchoring antigen selected from a sterol, 3β-cholesterylamine, cholesterol, a fatty acid, a triglyceride, a phospholipid, acetylated or non-acetylated glycerol, a sphingolipid, sphingosine, ceramide, a glycerolipid, a glycerophospholipid, glycerophosphoethanolamine and a steroid. In certain embodiments, the monosaccharide or oligosaccharide moiety is galactose-alpha-1,3-galactose (α-gal), L-rhamnose or Forssman disaccharide.

In certain embodiments, the cell surface anchoring antigen conjugate comprises a lipid moiety of the formula:

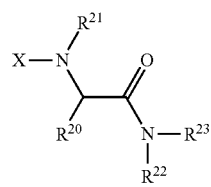

where X is a bond, —CO—, —O—CO— or —HNCO— and links the lipid moiety to an antigen;

$R^{20}$ is alkyl or alkenyl having 7-32 carbon atoms which are optionally substituted with 1-6 hydroxyl groups;

$R^{21}$ is hydrogen or an alkyl group;

$R^{22}$ and $R^{23}$ are independently hydrogen, or —CO—$R^{24}$, where $R^{24}$ is selected from hydrogen or alkyl having 1-6 carbon atoms which are optionally substituted with 1-6 hydroxyl groups.

In other embodiments, the general structure of the lipid moiety, or cell membrane anchoring portion of the molecule, is a cationic lipid where the conjugation is at the cationic end containing secondary, tertiary or quaternary amine group. FIG. 6 shows additional examples of cell membrane anchoring molecule/moiety (i.e., lipids).

Other molecules that can activate and/or boost the function of immune system and immune cells such as APC, B cells and T cells can also be incorporated into the formulation. Suitable immune function activating and/or boosting molecule can be selected from Granulocyte macrophage colony-stimulating factor (e.g. sargramostim or molgramostim), immunostimulatory monoclonal antibody (e.g. anti-KIR antibody such as lirilumab, antibody for CD137 such as urelumab or utomilumab), FMS-like tyrosine kinase 3 ligand (FLT3L), other pattern recognition receptor agonists besides poly IC, CpG and imiquimod, T-cell-tropic chemokines such as CCL2, CCL1, CCL22 and CCL17, B-cell chemoattractant such as CXCL13, Interferon gamma, type I IFN (e.g. IFN-a, IFN-beta), tumor necrosis factor (TNF)-beta, TNF-alpha, IL-1, interleukin-2 (IL-2 such as aldesleukin, teceleukin or bioleukin), interleukin-10 (IL-10), IL-12, IL-6, IL-24, IL-2, IL-18, IL-4, IL-5, IL-6, IL-9 and IL-13 or their derivatives such as PEGylated derivative, CD1d ligand, Vα14/Vβ8.2 T cell receptor ligand, iNKT agonist, α-galactosylceramide (α-GalCer), α-glucosylceramide (α-GlcCer), α-glucuronylceramide, α-galacturonylceramide, Isoglobotriosylceramide (iGb3) and HS44. The agents can be added to the formulation described herein at a therapeutically effective amount, to be used as an intratumoral injection.

It is contemplated that a cell surface anchoring antigen conjugate as described herein can be replaced with a therapeutic antibody, including a monoclonal antibody, bi-specific antibody and antibody-drug conjugates. Examples of therapeutic antibodies include herceptin, rituximab, bexxar, cetuximab, bevacizumab, panitumumab, pertuzumab, kadcyla and catumaxomab, antibody against tumor surface antigen such as GalNAc—O-Ser/Thr (Tn Antigen), Gal 1-3GalNAc—O-Ser/Thr (Core 1 antigen), STF antigen and the like. The antigen used in the conjugate need not to be highly tumor specific because the antibody can be injected into the tumor to reach high local concentration to be effective. For example, an antibody against epithelial cell adhesion molecule (EpCAM) antigen can be used for epithelia and epithelial-derived tumor cells although it also binds with other normal epithelial cells. These antibodies or an antibody-drug conjugates can be injected into solid tumor to lyse the tumor cell and/or improve the antigen presenting, therefore release neo antigen to promote immune response. Preferably these molecules and compositions are injected into the tumor together with an immune function enhancing agent and optionally with sialidase. Preferably the target tumor need to have expression of the antigen specific for the antibody, e.g. the tumor needs to be HER2+ for treatment using Herceptin and the tumor needs to be EGFR-expressing for treatment using cetuximab. A formulation as described herein may include one or more antibody type drug and an immune function enhancing agent and optionally sialidase at a therapeutically effective amount. In certain embodiments, formulations can be a suspension containing about 50 mg/mL herceptin and about 5 mg/mL imiquimod in combination with another pharmaceutical acceptable excipient. The antibodies can be mixed with other ingredient right before injection, therefore allowing the user to use commercially available antibodies. The user can use the formulation solution containing an immune function enhancing agent with optional sialidase as diluents to reconstitute lyophilized antibodies; or use antibody solutions as diluents to reconstitute the lyophilized formulation containing an immune function enhancing agent and sialidase.

Similarly, chemotherapy drugs can also be used in the present compositions and formulations, instead of the cell surface anchoring antigen conjugate or in combination of the cell surface anchoring antigen conjugate. Examples of these drugs include alkylating agents (such as cyclophosphamide, uramustine, carmustine and usulfan), antimetabolites (such as methotrexate and fluorouracil), anti-microtubule agents (such as paclitaxel, vindesine and vinflunine), topoisomerase inhibitors (such as irinotecan and topotecan) and cytotoxic antibiotics (such as anthracyclines, bleomycins, mitomycin C, mitoxantrone and actinomycin).

Methods

The disclosure also relates to methods of treating cancer. Accordingly, provided herein is a method of treating and/or inhibiting a solid tumor, comprising administering to a patient in need thereof a therapeutically effective amount of the cell surface anchoring antigen conjugate, a formulation or pharmaceutical composition as described herein. The cell surface anchoring antigen conjugate, a formulation or pharmaceutical composition as described herein can be injected intratumorally to treat the cancer. In certain embodiments, the cell surface anchoring antigen conjugate, a formulation or pharmaceutical composition further comprises a cancer cell binding domain to increase its targeting to cancer cell, which will allow intravenous (IV) injection instead of intratumoral injection. In certain embodiments, the treating and/or inhibiting comprises preventing metastasis of the tumor. In other embodiments, the method comprises administering a therapeutically effective amount of an immune check point inhibitor, such as T lymphocyte antigen 4 (CTLA4) blocking antibody, PD-1 blocking antibody, PD-L1 blocking antibody, ipilimumab, tremelimumab, atezolizumab, nivolumab or pembrolizumab, or a combination thereof.

As employed herein, the phrase "an effective amount," refers to a dose sufficient to provide concentrations high enough to impart a beneficial effect on the recipient thereof. The specific therapeutically effective dose level for any particular subject will depend upon a variety of factors including the disorder being treated, the severity of the disorder, the activity of the specific compound, the route of administration, the rate of clearance of the compound, the duration of treatment, the drugs used in combination or coincident with the compound, the age, body weight, sex, diet, and general health of the subject, and like factors well known in the medical arts and sciences. Various general considerations taken into account in determining the "therapeutically effective amount" are known to those of skill in the art and are described. Dosage levels typically fall in the range of about 0.001 up to 100 mg/kg; with levels in the range of about 0.05 up to 10 mg/kg are generally applicable.

The cell surface anchoring antigen conjugate, a formulation or pharmaceutical composition as described herein can be administered parenterally, such as intravascularly, intravenously, intraarterially, intramuscularly, subcutaneously, or the like. Administration can also be orally, nasally, rectally, transdermally or inhalationally via an aerosol. A therapeutically effective dose can be estimated initially from cell culture assays by determining an $IC_{50}$. A dose can then be formulated in animal models to achieve the $IC_{50}$ as determined in cell culture. Such information can be used to more accurately determine useful initial doses in humans. Levels of drug in plasma or tumor may be measured, for example, by HPLC. The exact formulation, route of administration and dosage can be chosen by the individual physician in view of the patient's condition. Compounds described herein can be administered as a pharmaceutical or medicament formulated with a pharmaceutically acceptable carrier. Accordingly, the compounds may be used in the manufacture of a medicament or pharmaceutical composition. Pharmaceutical compositions may be formulated as solutions or lyophilized powders for parenteral administration. Powders may be reconstituted by addition of a suitable diluent or other pharmaceutically acceptable carrier prior to use. Liquid formulations may be buffered, isotonic, aqueous solutions. Powders also may be sprayed in dry form. Examples of suitable diluents are saline solution (either isotonic or non-isotonic), standard 5% dextrose in water, or buffered sodium or ammonium acetate solution. Such formulations are especially suitable for parenteral administration. Compounds may be formulated to include other medically useful drugs or biological agents. The compounds also may be administered in conjunction with the administration of other drugs or biological agents useful for the disease or condition to which the compounds are directed.

Another agent that can be injected to the tumor (e.g., melanoma) to treat cancer is sialidase or sialidase conjugated with cholesterylamine or lipid type molecule. It can increase the cytotoxicity of NK cell, antigen presenting and antibody mediated complement activation against tumor cells. The sialidase can be either bacterial sialidase or viral sialidase or animal sialidase or human sialidase in therapeutically effective amounts (e.g. 0.1~10 mg per injection). It can be either in monomer or oligomer or polymer (e.g. conjugated to a soluble polymer backbone) or coated on nano/micro particles. Preferably it is injected together with the cancer cell lysing agent into the tumor at therapeutically effective amounts. It can also be co-formulated with the immune function enhancing agent type agent.

The cell surface anchoring antigen conjugate, a formulation or pharmaceutical composition as described herein can be administered in the form of active drug, prodrug, liposome, micelle, sustained release formulation, conjugated to polymer drug carrier (e.g. dextran) or encapsulated in biodegradable micro particle/nano particle, etc. The amount and concentration should be sufficient to lyse a significant amount of the cancer cells (e.g. >5% of the cancer cells in the tumor being injected). Cell lysing peptides and antibiotics, such as polymyxin, can be also be used in the formulations and compositions described herein. Other agents that can lyse the cancer cell when being intratumorally injected can be also be used in combination with the cell surface anchoring antigen conjugate in compositions and formulations described herein. For example, the formulation may comprise an acid or base (e.g., 0.1~1M, pH=2 in an organic acid buffer, such as lactic acid or citric acid, or 0.1~1M pH=10 in a $Na_2CO_3$ buffer), organic solvent (e.g., 75% ethanol, DMF, DMSO, acetone), perforin, C3b, C5b, membrane attack complex, cytotoxic T cells, NK cells and a cell lysing detergent/surfactant.

The cell surface anchoring antigen, antibody, chemotherapy drug, cell lysing peptide or antibiotic, and detergent described herein work as a cancer cell lysing agent and are capable of enhancing the presentation of antigens on a tumor. The amount and concentration should be sufficient to lyse a significant amount of the cancer cells (e.g. >10% of the cancer cells in the tumor being injected). The current invention discloses composition and formulation to treat cancer. The composition or formulation comprises cancer cell lysing agent and immune function enhancing agent in a pharmaceutical acceptable carrier that can be used as intratumoral injection to treat cancer.

They can be either in the form of active drug, prodrug, liposome, micelle, sustained release formulation, conjugated to polymer drug carrier (e.g. dextran) or encapsulated in biodegradable micro particle/nano particle. The preferred amount and concentration should be enough to lyse significant amount of the cancer cells (e.g. >10% of the cancer cells in the tumor being injected). Examples of the detergent that can be used include anionic detergents, cationic detergents, non-ionic detergents and zwitterionic detergents such as alkylbenzenesulfate, alkylbenzenesulfonates, bile acids, deoxycholic acid, quaternary ammonium type detergents, tween, triton, CHAPS, SLS, SDS, SLES, DOC, NP-40, cetrimonium bromide (CTAB), cetylpyridinium chloride (CPC), benzalkonium chloride (BAC), benzethonium chloride (BZT), dimethyldioctadecylammonium chloride and dioctadecyldimethylammonium bromide (DODAB), as long as they can effectively lyse the tumor cell in vivo. For example, they can be injected at a concentration between 0.1 about 100 mg/mL.

Also provided are methods of inhibiting or eliminating cancer cells in a tumor and/or preventing metastasis. The method comprises administering to a patient in need thereof a formulation or composition as described herein, which comprises a cancer cell lysing agent, such as cell surface anchoring antigen conjugate, in combination with an immune function enhancing agent. The composition may be administered via intratumoral injection to the tumor. The immune function enhancing agent can be given to the patient by intratumoral injection as a mixture with the cancer cell lysing agent, such as a cell surface anchoring antigen conjugate, or sequentially (before or after) to the same tumor injected with a cancer cell lysing agent. For example, a liquid formulation containing both a cancer cell lysing agent and an immune function enhancing agent can be injected into the tumor (e.g., at 50 µL to about 1,000 µL/cm³ tumor volume. The tumor be any type of solid tumor, provided it allows intratumoral injection.

In addition, immune checkpoint inhibitors at therapeutically effective amounts could be administered to further enhance this treatment. The immune checkpoint inhibitor can be administered as an intratumoral injection or via IV injection.

Examples of suitable immune check point inhibitors include an antibody against PD-1, an antibody against PD-L1, an antibody against CTLA-4, or a combination thereof examples include ipilimumab, tremelimumab, atezolizumab, nivolumab and pembrolizumab. For example, the patient can be intravenously injected with ipilimumab (e.g., at a dose of from about 3 to about 10 mg/kg every 3 weeks for 4 doses after treatment or atezolizumab 1200 mg IV every three weeks after treatment until disease progression).

In summary, provided are methods to kill cancers cells in a tumor and/or to prevent or delay metastasis by treating a primary tumor. The method comprises administering to a patient in need thereof, a cancer cell lysing agent optionally in combination with an immune function enhancing agent. Immune checkpoint inhibitors at therapeutically effective amounts can also be administered to further enhance this treatment. The immune function enhancing agent is administered by intratumoral injection to the primary tumor. It can be administered to a subject in need thereof by intratumoral injection as a mixture with a cancer cell lysing agent or sequentially (before or after) to the same tumor injected with the cancer cell lysing reagent. The treatment to the primary tumor will induce an immune response against distant and secondary tumor to kill the cancer cells within, as well as prevent the metastasis of tumor. The composition used for intratumoral injection comprises a cancer cell lysing agent and an immune function enhancing agent in a pharmaceutical acceptable carrier. The formulation comprises a cancer cell lysing agent and an immune function enhancing agent in a pharmaceutical acceptable carrier. It can be injectable liquid or solid dosage form, such as a lyophilized formulation, that can be reconstituted with an injectable liquid. The cancer cell lysing agent and immune function enhancing agent can be in the form of an active drug, prodrug, liposome, micelle, emulsion, gel, implant, thermal phase changing formulation, insoluble precipitate (e.g. in complex with condensing reagent), conjugated to polymer drug carrier (e.g. dextran), coated on the surface or encapsulated within biodegradable micro particle or nanoparticle. A thermal phase changing formulation is a formulation that changes its phase from a liquid to a semisolid when the temperature increases. Such formulations typically use poloxamer as an excipient. Exemplary sizes of the microparticles or nanoparticles is between 10 nm and 100 µm.

Also provided is a composition comprising a cell surface anchoring antigen conjugate as described herein and an immune function enhancing agent. Such compositions can be injected into the tumor (e.g., at 50 µL to about 1000 µL/cm³ tumor volume). Examples of suitable immune function enhancing agents include PRR Ligands, TLR3 Ligands, RLR Ligands, TLR4 Ligands, TLR5 Ligands, TLR7/8 Ligands, TLR9 Ligands, NOD2 Ligands, imidazoquinoline family of TLR7/8 Ligands (e.g. imiquimod (R837), gardiquimod, resiquimod (R848), 3M-052, 3M-852, 3M-S-34240), CpG ODNs (CpG oligodeoxynucleotide) such as ODN 1826 and ODN 2216, synthetic analogs of dsRNA, such as poly IC (e.g. Poly ICLC, poly IC-Kanamycin, PolyI:PolyC12U), TLR4/5 Ligands such as Bacterial lipopolysaccharides (LPS, e.g. monophosphoryl lipid A), bacterial flagellin (e.g. *Vibrio vulnificus* flagellin B) or their derivatives, or their combinations. Many are commercially available (e.g. Invivogen).

The immune function enhancing agents can be administered as a prodrug, liposome, emulsion, micelle, sustained release formulation, insoluble precipitate (e.g. in complex with condensing reagent), conjugated to polymer drug carrier (e.g. dextran) or encapsulated in biodegradable micro particle/nano particle (e.g. those made of biodegradable polymer such as PLA, PLGA, PCL, PGA or PHB). The use and preparation of vaccine adjuvants encapsulated micro particle/nano particle or its prodrug are well known to the skilled in the art. Examples can be found in or adopted from Vaccine, 2014, 32(24), 2882-95; Science, 2015, 348(6241), aaa8205 and Nat Commun., 2016, 7, 13193, as well as US patent application U.S. Ser. No. 13/560,955, U.S. Ser. No. 12/764,569 and U.S. Ser. No. 12/788,266.

In certain embodiments, the immune function enhancing agent-containing compositions are given intratumorally at therapeutically effective amounts. For example, the imiquimod can be given at the amount between 1 and about 100 mg as free drug or given as 10 mg to about mg micro or nano particle encapsulating imiquimod. Other suitable dosing can be used, as long as it can produce a satisfactory therapeutic effect, which can be determined experimentally by screening and testing with well-known protocol and methods.

Synthesis of the Cell Surface Anchoring Antigen Conjugates

The 3β-cholesterylamine, or a derivative thereof, and antigens used in the cell surface anchoring antigen conjugates described herein may be isolated using known methods, purchased from a commercial source or partially or fully synthesized using methods well known in the art (e.g., chemical and/or biotechnological methods).

In certain embodiments, cell surface anchoring antigen conjugates may be formed by covalently bonding the antigen by use of a linker, to the 3β-cholesterylamine through the formation of one or more amide, amino or imino bonds between an acid, aldehyde, amino, or hydrazo group on the 3β-cholesterylamine. All of these methods are known in the art. See, e.g., Hermanson G. T., Bioconjugate Techniques, Academic Press, pp. 169-186 (1996), incorporated herein by reference. As shown in Scheme 1, in one embodiment, the antigen can be covalently bound to a linker via the anomeric carbon atom. The linker has a leaving group (LG). This pre-conjugate can then be covalently bonded to the cholesterylamine to provide the cell surface anchoring antigen conjugates described herein.

cose. Other well-known pharmaceutically acceptable liquid carriers such as alcohols, glycols, esters and amides, may be employed. In certain embodiments, the composition further comprises one or more excipients, such as, but not limited to ionic strength modifying agents, solubility enhancing agents, sugars such as mannitol or sorbitol, pH buffering agent, surfactants, stabilizing polymer, preservatives, and/or co-solvents.

In certain embodiments, a polymer matrix or polymeric material is employed as a pharmaceutically acceptable carrier. The polymeric material described herein may comprise natural or unnatural polymers, for example, such as sugars, peptides, protein, laminin, collagen, hyaluronic acid, ionic and non-ionic water soluble polymers; acrylic acid polymers; hydrophilic polymers such as polyethylene oxides, polyoxyethylene-polyoxypropylene copolymers, and polyvinylalcohol; cellulosic polymers and cellulosic polymer derivatives such as hydroxypropyl cellulose, hydroxyethyl cellulose, hydroxypropyl methylcellulose, hydroxypropyl methylcellulose phthalate, methyl cellulose, carboxymethyl cellulose, and etherified cellulose; poly(lactic acid), poly (glycolic acid), copolymers of lactic and glycolic acids, or other polymeric agents both natural and synthetic. In certain

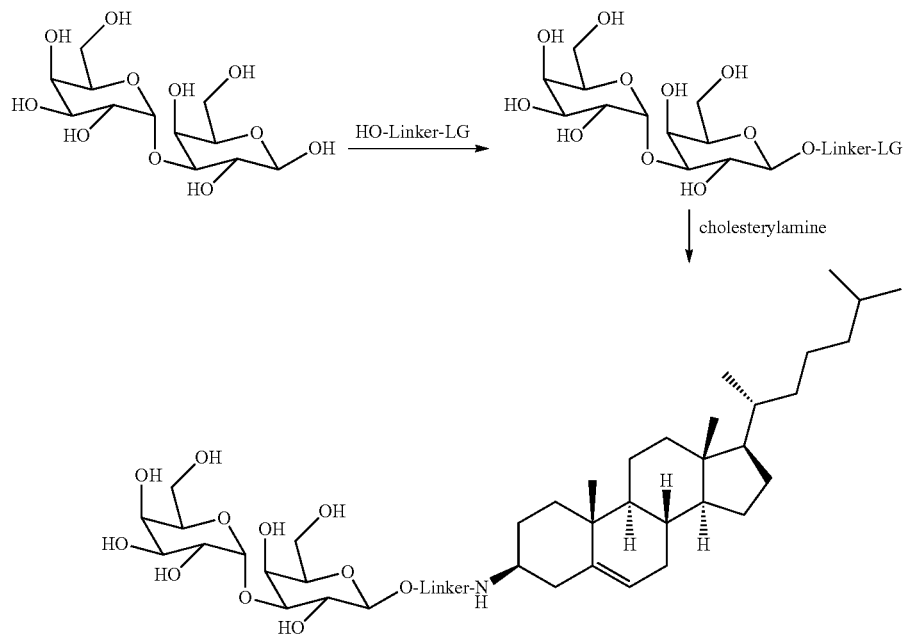

Scheme 1

Pharmaceutical Compositions

The present disclosure provides compositions which typically comprise at least one pharmaceutically acceptable carrier. Pharmaceutically acceptable carriers are known to one having ordinary skill in the art may be used, including water or saline. As is known in the art, the components as well as their relative amounts are determined by the intended use and method of delivery. The compositions provided in accordance with the present disclosure are formulated as a solution for delivery into a patient in need thereof, and are, in particular, focused on intravenous delivery.

Diluent or carriers employed in the compositions can be selected so that they do not diminish the desired effects of the composition. Examples of suitable compositions include aqueous solutions, for example, a saline solution, 5% gluembodiments, compositions provided herein may be formulated as films, gels, foams, or and other dosage forms.

Suitable ionic strength modifying agents include, for example, glycerin, propylene glycol, mannitol, glucose, dextrose, sorbitol, sodium chloride, potassium chloride, and other electrolytes.

In certain embodiments, the solubility of the cell surface anchoring antigen conjugates may need to be enhanced. In such cases, the solubility may be increased by the use of appropriate formulation techniques, such as the incorporation of solubility-enhancing compositions such as mannitol, ethanol, glycerin, polyethylene glycols, propylene glycol, poloxomers, and others known in the art.

Suitable pH buffering agents for use in the compositions herein include, for example, acetate, borate, carbonate, citrate, and phosphate buffers, as well as hydrochloric acid, sodium hydroxide, magnesium oxide, monopotassium phosphate, bicarbonate, ammonia, carbonic acid, hydrochloric acid, sodium citrate, citric acid, acetic acid, disodium hydrogen phosphate, borax, boric acid, sodium hydroxide, diethyl barbituric acid, and proteins, as well as various biological buffers, for example, TAPS, Bicine, Tris, Tricine, HEPES, TES, MOPS, PIPES, cacodylate, or MES. In certain embodiments, an appropriate buffer system (e.g., sodium phosphate, sodium acetate, sodium citrate, sodium borate or boric acid) is added to the composition to prevent pH drift under storage conditions. In some embodiments, the buffer is a phosphate buffered saline (PBS) solution (i.e., containing sodium phosphate, sodium chloride and in some formulations, potassium chloride and potassium phosphate). The particular concentration will vary, depending on the agent employed. In certain embodiments, the pH buffer system (e.g., sodium phosphate, sodium acetate, sodium citrate, sodium borate or boric acid) is added to maintain a pH within the range of from about pH 4 to about pH 8, or about pH 5 to about pH 8, or about pH 6 to about pH 8, or about pH 7 to about pH 8. In some embodiments, the buffer is chosen to maintain a pH within the range of from about pH 2 to about pH 11. In some embodiments, the pH is from about pH 5 to about pH 8. In some embodiments, the buffer is a saline buffer. In certain embodiments, the pH is from about pH 4 and about pH 8, or from about pH 3 to about pH 8, or from about pH 4 to about pH 7.

Surfactants can be employed in the composition to deliver higher concentrations of cell surface anchoring antigen conjugates and immune function enhancing agents. The surfactants function to solubilize the insoluble and stabilize colloid dispersion, such as micellar solution, microemulsion, emulsion and suspension. Suitable surfactants comprise polysorbate, poloxamer, polyosyl 40 stearate, polyoxyl castor oil, tyloxapol, triton, and sorbitan monolaurate. In one embodiment, the surfactants have hydrophile/lipophile/balance (HLB) in the range of 12.4 to 13.2 and are acceptable for ophthalmic use, such as TritonX114 and tyloxapol.

The compositions described herein may be sterilized to remove unwanted contaminants including, but not limited to, endotoxins and infectious agents. Sterilization techniques which do not adversely affect the structure and biotropic properties of the cell surface anchoring antigen conjugates can be used. In certain embodiments, the composition can be disinfected and/or sterilized using conventional sterilization techniques including propylene oxide or ethylene oxide treatment, sterile filtration, gas plasma sterilization, gamma radiation, electron beam, and/or sterilization with a peracid, such as peracetic acid. In one embodiment, the composition can be subjected to one or more sterilization processes. Alternatively, the composition may be wrapped in any type of container including a plastic wrap or a foil wrap, and may be further sterilized.

In some embodiments, preservatives are added to the composition to prevent microbial contamination during use. Suitable preservatives added to the anti-adhesion compositions comprise benzalkonium chloride, benzoic acid, alkyl parabens, alkyl benzoates, chlorobutanol, chlorocresol, cetyl alcohols, fatty alcohols such as hexadecyl alcohol, organometallic compounds of mercury such as acetate, phenylmercury nitrate or borate, diazolidinyl urea, diisopropyl adipate, dimethyl polysiloxane, salts of EDTA, vitamin E and its mixtures. In certain embodiments, the preservative is selected from benzalkonium chloride, chlorobutanol, benzododecinium bromide, methyl paraben, propyl paraben, phenylethyl alcohol, edentate disodium, sorbic acid, or polyquarternium.

In some embodiments, separate or sequential administration of the composition and other agent is necessary to facilitate delivery of the composition into the patient. In certain embodiments, the composition and the other agent can be administered at different dosing frequencies or intervals. For example, one composition can be administered daily or weekly, while the other agent can be administered less frequently. Additionally, as will be apparent to those skilled in the art, the composition and the other agent can be administered using the same route of administration or different routes of administration.

Any effective regimen for administering the composition can be used. For example, the composition can be administered as a single dose, as an infusion. Further, a staggered regimen, for example, one to two days per week can be used as an alternative to daily treatment.

Formulations contemplated by the present disclosure may also be for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection, but less preferred in the context of the present disclosure. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the component in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

In making pharmaceutical compositions that include cell surface anchoring antigen conjugates described herein, the active ingredient is usually diluted by an excipient or carrier and/or enclosed within such a carrier that can be in the form of a capsule, sachet, paper or other container. When the excipient serves as a diluent, it can be a solid, semi-solid, or liquid material (as above), which acts as a vehicle, carrier or medium for the active ingredient. Thus, the compositions can be in the form of films, gels, powders, suspensions, emulsions, solutions, containing, for example, up to 10% by weight of the active compounds, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: wetting agents; emulsifying and suspending agents; and preserving agents such as methyl- and propylhydroxy-benzoates.

Gels are used herein refer to a solid, jelly-like material that can have properties ranging from soft and weak to hard and tough. As is well known in the art, a gel is a non-fluid colloidal network or polymer network that is expanded throughout its whole volume by a fluid. A hydrogel is a type of gel which comprises a network of polymer chains that are hydrophilic, sometimes found as a colloidal gel in which water is the dispersion medium. Hydrogels are highly absorbent and can contain a high degree of water, such as, for example greater than 90% water. In some embodiments, the gel described herein comprises a natural or synthetic polymeric network. In some embodiments, the gel comprises a hydrophilic polymer matrix. In other embodiments, the gel comprises a hydrophobic polymer matrix. In some embodiments, the gel possesses a degree of flexibility very similar to natural tissue. In certain embodiments, the gel is biocompatible and absorbable. In certain embodiments, the gel is administered to the patient prior to, during or after surgical intervention.

Liquid solution as used herein refers to solutions, suspensions, emulsions, drops, ointments, liquid wash, sprays, liposomes which are well known in the art. In some embodiments, the liquid solution contains an aqueous pH buffer agent which resists changes in 660 pH when small quantities of acid or base are added.

Alternatively, exemplary formulations may comprise: a) cell surface anchoring antigen conjugate and immune function enhancing agents as described herein; b) pharmaceutically acceptable carrier; and c) hydrophilic polymer as matrix network, wherein said compositions are formulated as viscous liquids, i.e., viscosities from several hundred to several thousand cps, gels or ointments. In these embodiments, the cell surface anchoring antigen conjugates is dispersed or dissolved in an appropriate pharmaceutically acceptable carrier.

In certain embodiments, the cell surface anchoring antigen conjugates or a composition comprising the same, is lyophilized prior to, during, or after, formulation. In certain embodiments, the cell surface anchoring antigen conjugates, or a composition comprising the same, is lyophilized in a pharmaceutical formulation comprising a bulking agent, a lyoprotectant, or a mixture thereof. In certain embodiments, the lyoprotectant is sucrose. In certain embodiments, the bulking agent is mannitol. In certain embodiments, the cell surface anchoring antigen conjugates, or a composition comprising the same, is lyophilized in a pharmaceutical formulation comprising mannitol and sucrose. Exemplary pharmaceutical formulations may comprise about 1-20% mannitol and about 1-20% sucrose. The pharmaceutical formulations may further comprise one or more buffers, including but not limited to, phosphate buffers. Accordingly, also provided herein is a lyophilized composition comprising a drug conjugate, nanoparticle or composition comprising the same as described herein.

Dosing

Suitable dosages can be determined by standard methods, for example by establishing dose-response curves in laboratory animal models or in clinical trials and can vary significantly depending on the patient condition, the disease state being treated, the route of administration and tissue distribution, and the possibility of co-usage of other therapeutic treatments. The effective amount to be administered to a patient is based on body surface area, patient weight or mass, and physician assessment of patient condition. In various exemplary embodiments, a dose ranges from about 0.0001 mg to about 10 mg. In other illustrative aspects, effective doses ranges from about 0.01 μg to about 1000 mg per dose, 1 μg to about 100 mg per dose, or from about 100 μg to about 50 mg per dose, or from about 500 μg to about 10 mg per dose or from about 1 mg to 10 mg per dose, or from about 1 to about 100 mg per dose, or from about 1 mg to 5000 mg per dose, or from about 1 mg to 3000 mg per dose, or from about 100 mg to 3000 mg per dose, or from about 1000 mg to 3000 mg per dose. In any of the various embodiments described herein, effective doses ranges from about 0.01 μg to about 1000 mg per dose, 1 μg to about 100 mg per dose, about 100 μg to about 1.0 mg, about 50 μg to about 600 μg, about 50 μg to about 700 μg, about 100 μg to about 200 μg, about 100 μg to about 600 μg, about 100 μg to about 500 μg, about 200 μg to about 600 μg, or from about 100 μg to about 50 mg per dose, or from about 500 μg to about 10 mg per dose or from about 1 mg to about 10 mg per dose. In other illustrative embodiments, effective doses can be about 1 μg, about 10 μg, about 25 μg, about 50 μg, about 75 μg, about 100 μg, about 125 μg, about 150 μg, about 200 μg, about 250 μg, about 275 μg, about 300 μg, about 350 μg, about 400 μg, about 450 μg, about 500 μg, about 550 μg, about 575 μg, about 600 μg, about 625 μg, about 650 μg, about 675 μg, about 700 μg, about 800 μg, about 900 μg, 1.0 mg, about 1.5 mg, about 2.0 mg, about 10 mg, about 100 mg, or about 100 mg to about 30 grams. In certain embodiments, the dose is from about 0.01 mL to about 10 mL.

In certain embodiments, the dose is administered to the subject in need thereof on daily basis as an injection. In other embodiments, the dose is given to the object once every 2-3 days as injection. In other illustrative embodiments, the dose is administered to the subject in need thereof once each week as an injection. In other embodiments, the dose is administered to the subject in need thereof once every two weeks as an injection. In other embodiments, the dose is administered to the subject in need thereof once every month as an injection. The treatment can be continued until the desired therapeutical effect is reached.

EXAMPLES

Exemplary compositions, formulations and preparations of micro/nano particles used in the compositions and formulations are as follows.

Example 1

In an aqueous media, from one to about 100 mg/mL cancer cell lysing agent (e. g. α-gal-cholesterylamine or L-rhamnose-cholesterylamine conjugate or their mixture at 1:1 molar ratio), 0.1~50 mg/mL TLR7/8 Ligands (e.g. imiquimod or gardiquimod or resiquimod), 0.1~50 mg/mL TLR3/RLR Ligands (e.g. dsRNA such as poly IC or polyI-CLC), 0.1~50 mg/mL TLR9 Ligands (e.g. CpG ODNs such as ODN 1826 or ODN 2216) and 0.1~50 mg/mL neuraminidase (Sialidase) from *Vibrio cholera* in 1×PBS and then being lyophilized to give the final formulation. In one example, the formulations contain 30 mg/mL cancer cell lysing agent (e. g. α-gal-cholesterylamine or L-rhamnose-cholesterylamine conjugate), 5 mg/mL imiquimod, 5 mg/mL poly IC, 5 mg/mL class A CpG ODN 2216 and 5 mg/mL neuraminidase (Sialidase) from *Vibrio cholera* in 1×PBS and 5% sucrose. It can be injected to the tumor at 100 μL~300 μL/cm³ tumor size after being reconstituted with water.

Example 2

In an aqueous media, 100 mg/mL cancer cell lysing agent (e. g. α-gal-cholesterylamine or L-rhamnose-cholesterylamine conjugate), 2 mg/mL imiquimod, 2 mg/mL poly IC, 2 mg/mL class A CpG ODN 2216 or class B CpG ODN and 2 mg/mL neuraminidase (Sialidase)-lipid conjugate in 1×PBS and 15% mineral oil to form an emulsion. The drugs in the above embodiments are in active form, one or more or all of them can also be in the form of prodrug, liposome, micelle, insoluble precipitate (e.g. in complex with condensing reagent), conjugated to polymer drug carrier (e.g. dextran) or coated on or encapsulated in biodegradable micro particle/nano particle as previously described. For example, compounds having one or more amine groups that can precipitate poly IC and CpG ODN therefore generate insoluble precipitates can be used as sustained release drug formulations. Examples of said co-precipitation compound include α-polylysine, ε-polylysine, spermine, polymyxin, gentamycin, nisin, DC-Cholesterol, cholesterylamine, tertiary/quaternary ammonium type detergents (e.g. cetrimonium salt, cetylpyridinium salt, benzalkonium chloride, benzethonium chloride, dimethyldioctadecylammonium chloride and dioctadecyldimethylammonium salt) or their base form. Imiquimod or gardiquimod or resiquimod can also form precipitation with poly IC or CpG ODN. Surfactant can be added to the precipitates to from stable suspension.

Example 3

Encapsulation of poly IC or CpG ODN in biodegradable micro or nano sphere can be performed by the addition of amine containing compounds described herein. For example, PLGA-hybrid nanospheres encapsulating poly IC or CpG ODN is prepared using a double emulsion-solvent evaporation method. Briefly, 1 ml poly IC or CpG ODN in Tris/EDTA buffer is emulsified in a PLGA solution (5% w/v in methylene chloride, MW=66,000 Da; Birmingham Polymers, Birmingham, Ala., USA) with DC-Cholesterol or cetyldimethylamine or gardiquimod solution (5% w/v in methylene chloride) using a sonicator for 5 min. A water-in-oil solution is emulsified in 25 ml of 4% (w/v) aqueous polyvinyl alcohol (PVA, MW=30,000-70,000 Da; Sigma, St. Louis, Mo.) solution using a sonicator for 5 min. The emulsion is stirred for 72 h at room temperature to remove methylene chloride. PLGA nanospheres is recovered by ultracentrifugation (20,000 g for 20 min at 4° C.). The PLGA nanosphere pellet is washed five times in distilled water to remove PVA and was then re-suspended by vortexing and lyophilizing for 48 h to obtain a dry powder. When additional imiquimod (e.g. 1% w/v in methylene chloride) is added to the poly IC or CpG ODN solution, the resulting nanosphere will also encapsulate imiquimod. The prepared nanosphere can be used as an immune function enhancing agent.

Example 4

The nanosphere encapsulating poly IC and imiquimod can be prepared using a double emulsion water/oil/water system. Briefly, the PLGA is prepared at 10% wt/vol in $CH_2Cl_2$, which also contain 3% imiquimod and poly IC is prepared at 50 mg/mL in PBS. Emulsification via sonication is performed using a homogenizer and then a sonicator. The primary emulsion is carried out in a thick walled glass pressure tube with an aqueous to organic phase ratio of 1:5. Following a homogenization step, Emprove PVA 4-88 aqueous solution is added to the PLGA organic solution (at a volume ratio of 3:1 PVA to organic phase), vortex mixed, and emulsified by sonication. The resultant double emulsion is then transferred into a beaker under stirring containing 70 mM phosphate buffer pH 8.0 at a volume ratio of 1 part double emulsion to 7.5 parts buffer. The organic solvent (CH2Cl2) is allowed to evaporate for 2 h under stirring, and the nanoparticles are recovered via centrifugation at 75,600 rcf with two wash steps. PBS is used for the wash solutions and the final resuspension media. The washed suspension is stored at −20° C.

Example 5

A solution containing 20~200 mg/mL L-rhamnose-cholesterylamine conjugate, 3 mg/mL poly IC or 3 mg CpG ODN 2216 or both, 20 mg/mL biodegradable PLGA nano particles encapsulating 20% imiquimod, and granulocyte-monocyte colony-stimulating factor (10-200 μg/mL) is prepared. Suitable amount of surfactant can be added to from stable suspension. After the patient receive the intratumoral injection with the above formulation at 0.5 mL/cm$^3$ tumor volume, the patient is intravenously injected with Ipilimumab 3~10 mg/kg every 3 weeks for 4 doses, or Atezolizumab 1200 mg IV every 3 weeks until disease progression.

Example 6

A solution containing 100~200 mg/mL DNP-lipid conjugate with optionally 100 mg/mL α-gal-cholesterylamine conjugate, 10 mg/mL imiquimod, 2 mg/mL poly IC, 2 mg/mL CpG ODN 2216, 50 μg/mL granulocyte-monocyte colony-stimulating factor, 1×10$^4$-1×10$^5$U/mL of IFN-α, 1-10 MIU/mL IL-2 is prepared. After the patient receive the intratumoral injection with the above formulation, the patient is intravenously injected with Ipilimumab 3~10 mg/kg every 3 weeks for 4 doses, or Atezolizumab 1200 mg IV q3 wk until disease progression.

Example 7

A solution containing 100~200 mg/mL PLGA nano particles encapsulating 20% DNP-cholesterylamine conjugate, 2 mg/mL poly IC, 2 mg/mL CpG ODN 2216, 5 mg imiquimod, 0.5-2 mg/mL α-GalCer, 25×10$^4$U/mL of IFN-α, 5 MIU/mL IL-2 is prepared. After the patient receive the intratumoral injection with the above formulation at 0.3 mL/cm3 tumor volume, the patient is intravenously injected with Ipilimumab 3~10 mg/kg every 3 weeks for 4 doses, or Atezolizumab 1200 mg IV q3 wk until disease progression.

Example 8

A solution containing 100~200 mg/mL PLGA nano particles encapsulating 20% DNP-cholesterylamine conjugate, 2 mg/mL poly IC, 2 mg/mL CpG ODN 2216, 5 mg 3M-052, 5 MIU/mL IL-2 is prepared. After the patient receive the intratumoral injection with the above formulation at 0.6 mL/cm3 tumor volume, the patient is intravenously injected with Ipilimumab 3~10 mg/kg every 3 weeks for 4 doses, or Atezolizumab 1200 mg IV q3 wk until disease progression.

Example 9

A formulation containing 20~100 mg/mL Herceptin, 2 mg/mL imiquimod, 2 mg/mL poly IC, 5 mg/mL α-GalCer and 2 mg/mL neuraminidase (Sialidase, human) in 1×PBS is prepared. It can be injected into the Her2 positive tumor at 100~500 uL/cm3 tumor volume to treat cancer every 10 days for total 3 times. Check point inhibitor can be given to the patient at the same time and later.

Example 10

A formulation containing 50 mg/mL Herceptin with optional 50 mg/mL Cetuximab, 1 mg/mL imiquimod and 2 mg/mL neuraminidase in pharmaceutical acceptable excipient is prepared. In another example, the formulation contains 50 mg/mL Trastuzumab emtansine, mg/mL PLGA nanoparticle containing 10% imiquimod and 2 mg/mL poly IC in pharmaceutical acceptable excipient.

Example 11

A formulation containing 50 mg/mL Cetuximab, 2-5 mg/mL imiquimod and 2 mg/mL neuraminidase (*Vibrio cholera*) in PBS is prepared. In another example, the formulation contains mg/mL Cetuximab, 20 mg/mL PLGA nanoparticle containing 10% imiquimod, 2 mg/mL poly IC, 50 µg/mL granulocyte-monocyte colony-stimulating factor, $1 \times 10^4$-$1 \times 10^5$ U/mL of IFN-α, 1-10 MIU/mL IL-2 in pharmaceutical acceptable excipient. These Cetuximab containing formulations can be injected into EGFR-expressing tumor at 100~500 uL/cm3 tumor volume to treat cancer every 10 days for total 3 times. Check point inhibitor can be given to the patient at the same time and later.

Example 12

PLGA-R837 nanoparticles (R837 encapsulated in Poly Lactide-co-Glycolide particles) can be prepared using oil in water single-emulsion method. Briefly, R837 (TLR7 ligand) is dissolved in DMSO at 2.5 mg/ml. A total of 50 µL R837 is added to 1 ml PLGA (5 mg/ml) dissolved in dichloromethane. Next, the mixture is homogenized with 0.4 ml 5% w/v PVA solution for 10 min using ultrasonication. The oil in water emulsion is added to 2.1 ml of a 5% w/v solution of PVA to evaporate the organic solvent for 4 h at room temperature. PLGA-R837 nanoparticles are obtained after centrifugation at 3,500 g for 20 min.

Example 13

The immune function enhancing agent and a cell surface anchoring antigen conjugate can also be encapsulated together in micro/nano particles. For example, R837 or R848 is dissolved in DMSO at 2.5 mg/mL. A cell surface anchoring antigen conjugate as described herein is dissolved in DMSO at 50 mg/mL. 50 µL R837/R848 and 50 µL cell surface anchoring antigen conjugate solutions in DMSO are added to 1 mL mPEG-PLGA (10 mg/ml) dissolved in acetonitrile. Next, the mixture was dropwise added into 5 mL water containing 100 mg poly IC. After 1 h stirring and 12 h standing, the nanoparticles are obtained after centrifugation at 22,000 g for 5 min.

The invention claimed is:

1. A pharmaceutical composition comprising a cell surface anchoring antigen conjugate and a Toll-like receptors (TLR) agonist selected from a group consisting of poly IC, imiquimod or a mixture thereof, wherein the cell surface anchoring antigen conjugate contains a 3β-cholesterylamine moiety and a galactose-alpha-1,3-galactose (α-gal) moiety as antigen of pre-existing endogenous anti α-gal antibody, having a formula:

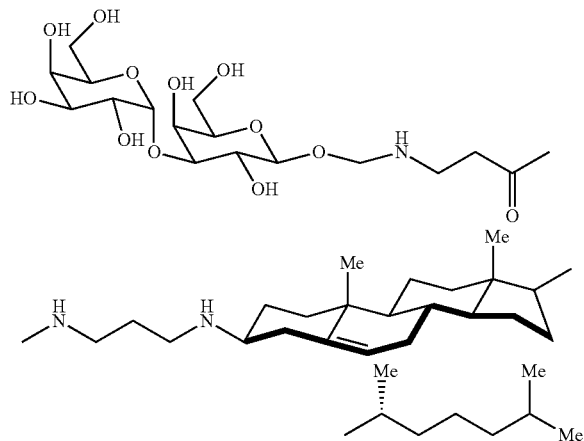

or a pharmaceutically acceptable salt thereof.

2. The pharmaceutical composition of claim 1, wherein the Toll-like receptors agonist is encapsulated in a particle.

3. The pharmaceutical composition of claim 1, wherein the cell surface anchoring antigen conjugate further comprises more than one copies of α-gal.

4. A pharmaceutical composition comprising a cell surface anchoring antigen conjugate and a Toll-like receptors (TLR) agonist selected from a group consisting of poly IC, imiquimod or a mixture thereof, wherein the cell surface anchoring antigen conjugate is a conjugate of L-rhamnose with 3β-cholesterylamine having formula:

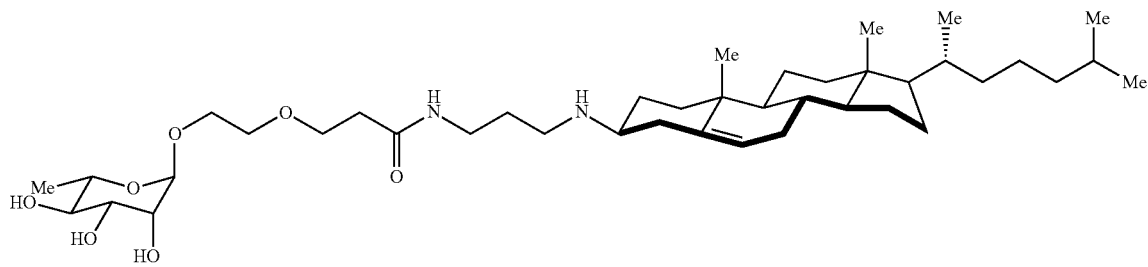

or a pharmaceutically acceptable salt thereof.

5. The pharmaceutical composition of claim 4, wherein the Toll-like receptors agonist is encapsulated in a particle.

6. The pharmaceutical composition of claim 4, wherein the cell surface anchoring antigen conjugate further comprises more than one copies of L-rhamnose.

\* \* \* \* \*